US009376359B2

(12) United States Patent
Mahieux et al.

(10) Patent No.: US 9,376,359 B2
(45) Date of Patent: Jun. 28, 2016

(54) PROCESS FOR PREPARING A PARA-LINEAR ALKYL-SUBSTITUTED HYDROXYAROMATIC COMPOUND

(71) Applicants: Cedrick Mahieux, Vallejo, CA (US); Curtis B. Campbell, Contra Costa, CA (US); Alexander E. Kuperman, San Ramon, CA (US)

(72) Inventors: Cedrick Mahieux, Vallejo, CA (US); Curtis B. Campbell, Contra Costa, CA (US); Alexander E. Kuperman, San Ramon, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 162 days.

(21) Appl. No.: 14/069,271

(22) Filed: Oct. 31, 2013

(65) Prior Publication Data

US 2015/0119308 A1   Apr. 30, 2015

(51) Int. Cl.
*C07C 37/08* (2006.01)
*C10M 129/10* (2006.01)

(52) U.S. Cl.
CPC .............. *C07C 37/08* (2013.01); *C10M 129/10* (2013.01); *C10M 2207/023* (2013.01)

(58) Field of Classification Search
CPC ............ C07C 37/08; C10M 2207/023; C10M 129/10
See application file for complete search history.

(56) References Cited

U.S. PATENT DOCUMENTS

| 3,953,538 | A |   | 4/1976 | Boney |
|---|---|---|---|---|
| 4,154,967 | A | * | 5/1979 | Matsunaga et al. ........... 568/771 |
| 4,225,737 | A |   | 9/1980 | Mikulicz |
| 4,536,301 | A |   | 8/1985 | Malloy et al. |
| 4,816,185 | A |   | 3/1989 | Parker et al. |
| 5,004,841 | A |   | 4/1991 | Lee |
| 5,468,407 | A |   | 11/1995 | Frazier |
| 5,750,818 | A |   | 5/1998 | Mehlberg et al. |
| 6,054,419 | A |   | 4/2000 | Le Coent |
| 6,551,967 | B2 |   | 4/2003 | King et al. |
| 6,989,355 | B1 |   | 1/2006 | Campbell et al. |
| 2007/0265476 | A1 |   | 11/2007 | Dakka et al. |
| 2015/0119309 | A1 | * | 4/2015 | Mahieux et al. ............. 508/584 |

FOREIGN PATENT DOCUMENTS

JP      08176572 A  *  7/1996

OTHER PUBLICATIONS

P.F. Diamond, the analysis of (nC1-C12) p-alkylphenols by a thin-layer chromatographic method, Journal of Chromatography A, 1968, vol. 32, p. 419.*
Sigma-Aldrich, 4-Dodecylphenol, mixture of isomers, Sigma-alrich.com, Jun. 2010, 1 page.*
Council of Ministers (Health Effects of Selected Chemicals, vol. 4-5, p. 229, 1999).*

* cited by examiner

*Primary Examiner* — Rosalynd Keys
(74) *Attorney, Agent, or Firm* — M. Carmen & Associates, PLLC.

(57) ABSTRACT

Disclosed herein is a process for preparing an isomeric mixture comprising a major amount of a para-linear mono-alkyl-substituted hydroxyaromatic compound. The process involves the steps of: (a) providing an isomeric mixture comprising a major amount of a para-di(alkyl-substituted)aromatic compound; wherein a first alkyl substituent is a $C_3$ to $C_8$ alkyl moiety and a second alkyl substituent is a $C_{4+n}$ to $C_{8+n}$ linear alkyl moiety, wherein n is 0 to 42 and further wherein the second alkyl substituent is at least one carbon atom greater than the first alkyl substituent; (b) subjecting the isomeric mixture comprising a major amount of a para-di(alkyl-substituted)aromatic compound to oxidation conditions in the presence of an oxygen-containing source, thereby converting the first alkyl substituent which is a $C_3$ to $C_8$ alkyl moiety to a hydroperoxide-containing substituted moiety to produce an isomeric mixture comprising a major amount of a para-linear alkyl-substituted, hydroperoxide-containing substituted aromatic compound; and (c) converting the hydroperoxide-containing substituted moiety to a hydroxyl moiety thereby providing an isomeric mixture comprising a major amount of a para-linear mono-alkyl-substituted hydroxyaromatic compound.

21 Claims, No Drawings

PROCESS FOR PREPARING A PARA-LINEAR ALKYL-SUBSTITUTED HYDROXYAROMATIC COMPOUND

BACKGROUND OF THE INVENTION

1. Technical Field

The present invention generally relates to a process for preparing a para-linear mono-alkyl-substituted hydroxyaromatic compound.

2. Description of the Related Art

Long chain para-alkylphenols lead to high-performance surfactants that are widely used in the manufacturing of lubricating oil additives. It is well known to prepare alklylphenols by alkylating phenol with branched olefins over ionic exchange resin catalysts.

Studies have been conducted and found that the branched alkylphenols may be toxic. Accordingly, it is believed that the branched alkylphenols will eventually be unavailable to use because of their toxicity. Thus, there has been an effort to replace the branched alkylphenols with less harmful linear homologues. However, replacing the branched olefins with normal alpha olefins in the phenol alkylation reaction brings some regioselectivity issues as formation of the undesired ortho-isomer prevails. Although research has been conducted to methods to improve the para-isomer selectivity, to date the research has not been successful.

U.S. Pat. No. 3,953,538 discloses an alkylation process in which a stream of an olefinic material is mixed with an acid stream and polymerized to cause formation of a polymeric diluent for the high strength acid which is initially charged to the alkylation process.

U.S. Pat. No. 4,225,737 ("the '737 patent") discloses a process for the alkylation of an aromatic hydrocarbon with an olefin-acting alkylating agent. The process disclosed in the '737 patent involves (a) commingling an aromatic hydrocarbon and a first portion of the olefin-acting alkylating agent at alkylation reaction conditions in a first alkylation reaction zone in contact with a hydrofluoric acid catalyst; (b) separating the effluent from the first alkylation reaction zone into an acid phase and a hydrocarbon phase comprising alkylate and unreacted aromatic hydrocarbon; (c) commingling the hydrocarbon phase with a second portion of the olefin-acting alkylating agent at alkylation reaction conditions in a second alkylation reaction zone in contact with the acid phase transferred from the first to said second reaction zone by maintaining a pressure differential between the first and second zones of from about 5 to about 20 psig.; (d) separating the effluent from the second alkylation reaction zone into an acid phase and a hydrocarbon phase and recycling the former to the first alkylation reaction zone; and, (e) recovering an aromatic alkylation product from the last-mentioned hydrocarbon phase.

U.S. Pat. No. 4,536,301 ("the '301 patent") discloses a surfactant slug used to recover residual oil in subterranean reservoirs. The slug disclosed in the '301 patent comprises a mixture of (1) from about 1 to about 10% of a sulfonate of a mixture of mono- and dialkyl-substituted aromatic hydrocarbon which has been obtained by the alkylation of an aromatic hydrocarbon with an olefinic hydrocarbon in the presence of a hydrogen fluoride catalyst; (2) a lower alkyl alcohol which possesses from about 3 to about 6 carbon atoms; and (3) a nonionic cosurfactant comprising an ethoxylated n-alcohol which possesses from about 12 to about 15 carbon atoms.

U.S. Pat. No. 4,816,185 discloses reaction products of $C_9$-$C_{30}$ alkylbenzenes with styrene and sulfonated derivatives thereof and processes for preparing such products and derivatives. The sulfonate salts of reaction products are especially useful as detergents.

U.S. Pat. No. 5,750,818 discloses a process for the liquid phase alkylation in an alkylation reactor of a hydrocarbon substrate with an olefinic alkylating agent in the presence of an acid alkylation catalyst at least one hydrocarbon having a lower boiling point than the hydrocarbon substrate and with a substantial stoichiometric excess of the hydrocarbon substrate over the alkylating agent to form a liquid product mixture.

U.S. Pat. No. 6,054,419 discloses a mixture of alkyl aryl sulfonates of superalkalinized alkaline earth metals comprising (a) 50 to 85% by weight of a mono alkyl phenyl sulfonate with a C14 to C40 linear chain wherein the molar proportion of phenyl sulfonate substituent in position 1 or position 2 is between 0 and 13% and (b0 15 to 50% by weight of a heavy alkyl aryl sulfonate, wherein the aryl radical is phenyl or not, and the alkyl chains are either two linear alkyl chains with a total number of carbon atoms of 16 to 40, or one or a plurality of branched alkyl chains with on average a total number of carbon atoms of 15 to 48.

U.S. Pat. No. 6,551,967 discloses a low overbased alkaline earth metal alkylaryl sulfonate having a Total Base Number of from about 2 to about 30, a dialkylate content of 0% to about 25% and a monoalkylate content of about 75% to about 90% or more, wherein the alkylaryl moiety is alkyltoluene or alkylbenzene in which the alkyl group is a $C_{15}$-$C_{21}$ branched chain alkyl group derived from a propylene oligomer are useful as lubricating oil additives.

U.S. Pat. No. 6,989,355 discloses an under-neutralized alkylxylene sulfonic acid composition for enhanced oil recovery processes. The patent also discloses a method for enhancing the recovery of oil from a subterranean reservoir which method employs the under-neutralized alkylxylene sulfonic acid compositions. The under-neutralized alkylxylene sulfonic acid compositions are employed in an aqueous media. The method optionally employs suitable co-surfactants, such as alcohols, alcohol ethers, polyalkylene glycols, poly(oxyalkylene)glycols and/or poly(oxyalkylene)glycol ethers.

It is desirable to provide an improved process for preparing a para-linear alkyl-substituted hydroxyaromatic compound.

SUMMARY OF THE INVENTION

In accordance with a first embodiment of the present invention, there is provided a process for preparing an isomeric mixture containing a major amount of a para-linear mono-alkyl-substituted hydroxyaromatic compound, the process comprising the steps of:

(a) providing an isomeric mixture comprising a major amount of a para-di(alkyl-substituted)aromatic compound, wherein a first alkyl substituent is a $C_3$ to $C_8$ alkyl moiety and a second alkyl substituent is a $C_{4+n}$ to $C_{8+n}$ linear alkyl moiety, wherein n is 0 to 42 and further wherein the second alkyl substituent is at least one carbon atom greater than the first alkyl substituent;

(b) subjecting the isomeric mixture comprising a major amount of a para-di(alkyl-substituted)aromatic compound to oxidation conditions in the presence of an oxygen-containing source, thereby converting the first alkyl substituent which is a $C_3$ to $C_8$ alkyl moiety to a hydroperoxide-containing substituted moiety to produce an isomeric mixture comprising a major amount of a para-linear alkyl-substituted, hydroperoxide-containing substituted aromatic compound; and (c) converting the hydroperoxide-containing substituted moiety to a hydroxyl moiety thereby providing an isomeric mixture comprising a major amount of a para-linear mono-alkyl-substituted hydroxyaromatic compound.

In accordance with a second embodiment of the present invention, there is provided a process comprising the steps of:

(a) providing an isomeric mixture comprising a major amount of a para-di(alkyl-substituted)aromatic compound of formula I:

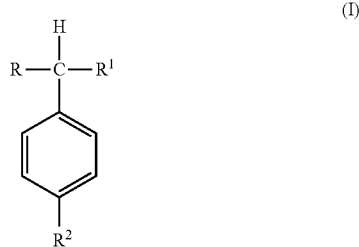

wherein R and $R^1$ are the same or different alkyl group such that the combined number of carbon atoms is no more than 8 carbon atoms, and $R^2$ is a linear alkyl group of from 4 to 50 carbon atoms, wherein $R^2$ is at least one carbon atom greater than the combined number of carbon atoms of R and $R^1$;

(b) subjecting the isomeric mixture comprising a major amount of the para-di(alkyl-substituted) aromatic compound of formula I to oxidation conditions in the presence of oxygen-containing source to produce an isomeric mixture comprising a major amount of a para-linear alkyl-substituted, hydroperoxide-containing substituted aromatic compound of formula II:

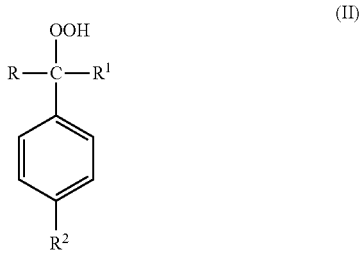

wherein R, $R^1$ and $R^2$ have the aforestated meanings; and (c) converting the hydroperoxide-containing substituted moiety of the para-linear alkyl-substituted, hydroperoxide-containing substituted aromatic compound of formula II to a hydroxyl moiety thereby providing an isomeric mixture comprising a major amount of a para-linear mono-alkyl-substituted hydroxyaromatic compound of formula III:

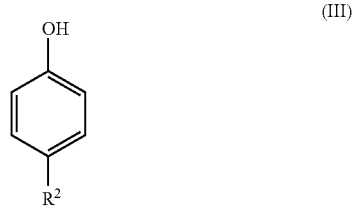

wherein $R^2$ has the aforestated meaning.

The process of the present invention advantageously provides an isomeric mixture comprising a major amount of a para-linear mono-alkyl-substituted hydroxyaromatic compound that can be prepared in a simple, cost efficient manner with a relatively low amount of ortho isomer formation. This is an unexpected improvement in that past efforts have not been able to produce such an isomeric mixture with a relatively low amount of the ortho isomer formation.

DETAILED DESCRIPTION OF THE PREFERRED EMBODIMENTS

Prior to discussing the invention in further detail, the following terms will be defined:

DEFINITIONS

As used herein, the following terms have the following meanings, unless expressly stated to the contrary:

The term "Total Base Number" or "TBN" as used herein refers to the amount of base equivalent to milligrams of KOH in 1 gram of sample. Thus, higher TBN numbers reflect more alkaline products, and therefore a greater alkalinity reserve. The TBN of a sample can be determined by ASTM Test No. D2896-11 issued May 15, 2011 or any other equivalent procedure.

The term "phenate" means a metal salt of a phenol.

The term "alkylphenate" means a metal salt of an alkylphenol.

The term "alkylphenol" means a phenol having an alkyl substituent which has a sufficient number of carbon atoms to impart oil solubility to the phenol.

The term "lime" refers to calcium hydroxide, also known as slaked lime or hydrated lime.

The term "metal" means alkali metals, alkaline earth metals, or mixtures thereof.

The term "alkaline earth metal" refers to calcium, barium, magnesium, and strontium.

The term "alkali metal" refers to lithium, sodium, potassium, rubidium, and cesium.

The term "metal base" refers to a metal hydroxide, metal oxide, metal alkoxides and the like and mixtures thereof, wherein the metal is an alkaline earth metal or alkali metal.

The term "overbased" refers to a class of metal salts or complexes. These materials have also been referred to as "basic", "superbased", "hyperbased", "complexes", "metal complexes", "high-metal containing salts", and the like. Overbased products are metal salts or complexes characterized by a metal content in excess of that which would be present according to the stoichiometry of the metal and the particular acidic organic compound reacted with the metal, e.g., a carboxylic acid. Suitable overbasing metals include alkaline earth metals such as magnesium, calcium, barium, and strontium. Suitable overbasing metals can be provided from the corresponding metal hydroxides, for example, calcium hydroxide and magnesium hydroxide provide the source for the alkaline earth metals calcium and magnesium, respectively. Additional overbasing can be achieved by the addition of acidic overbasing compounds for example, carbon dioxide and boric acid.

The terms "alkenyl succinic acid or anhydride" and "alkyl succinic acid or anhydride" may be used interchangeably.

The present invention is directed to a process for preparing an isomeric mixture comprising a major amount of a para-linear mono-alkyl-substituted hydroxyaromatic compound. In general, the process involves the steps of (a) providing an isomeric mixture comprising a major amount of a para-di (alkyl-substituted)aromatic compound; wherein a first alkyl substituent is a $C_3$ to $C_8$ alkyl moiety and a second alkyl substituent is a $C_{4+n}$ to $C_{8+n}$ linear alkyl moiety, wherein n is 0 to 42 and further wherein the second alkyl substituent is at least one carbon atom greater than the first alkyl substituent; (b) subjecting the isomeric mixture comprising a major amount of a para-di(alkyl-substituted)aromatic compound to oxidation conditions in the presence of an oxygen-containing source, thereby converting the first alkyl substituent which is a $C_3$ to $C_8$ alkyl moiety to a hydroperoxide-containing substituted moiety to produce an isomeric mixture comprising a major amount of a para-linear alkyl-substituted, hydroperoxide-substituted aromatic compound; and (c) converting the hydroperoxide-containing substituted moiety to a hydroxyl moiety thereby providing an isomeric mixture comprising a major amount of a para-linear mono-alkyl-substituted hydroxyaromatic compound.

In step (a), an isomeric mixture comprising a major amount of a para-di(alkyl-substituted)aromatic compound, wherein a first alkyl substituent is a $C_3$ to $C_8$ alkyl moiety and a second alkyl substituent is a $C_{4+n}$ to $C_{8+n}$ linear alkyl moiety, wherein n is 0 to 42 and further wherein the second alkyl substituent is at least one carbon atom greater than the first alkyl substituent is provided. In general, the isomeric mixture is obtained by alkylating a monoalkylaromatic compound with one or more linear alkylating agents in the presence of an acidic catalyst under reaction conditions sufficient to form a mixture of dialkylated benzenes which is, as noted hereinbefore, enriched in the para dialkylated benzene isomer and further enriched in the para-2-phenylalkane and para-3-phenylalkane isomers.

In general, the starting monoalkylaromatic compound may be obtained commercially. Suitable types of monoalkylaromatic compounds include, but are not limited to, cumene and the like and mixtures thereof. Alternatively, the starting monoalkylaromatic compound can be prepared by methods well known in the art, e.g., contacting benzene with a suitable alkylating agent under reaction conditions such that a monoalkylaromatic is formed. For example, the one or more alkylating agents may be propylene, butene, hexene or octene, thereby producing, respectively, cumene, butylbenzene, hexylbenzene, or octylbenzene.

The one or more linear alkylating agents for use in alkylating the monoalkylaromatic compound may include one or more normal alpha olefins. Suitable normal alpha olefins include, but are not limited to, 1-hexene, 1-nonene, 1-decene, 1-dodecene and the like and mixtures thereof. In one embodiment, the one or more linear alkylating agents is a mixture of normal alpha olefins selected from olefins having from about 10 to about 30 carbon atoms per molecule. In one embodiment, the one or more linear alkylating agents is a mixture of normal alpha olefins selected from olefins having from about 12 to about 30 carbon atoms per molecule. In one embodiment, the one or more linear alkylating agents is a mixture of normal alpha olefins selected from olefins having from about 18 to about 30 carbon atoms per molecule. In one embodiment, the one or more linear alkylating agents is a mixture of normal alpha olefins selected from olefins having from about 20 to about 24 carbon atoms per molecule.

Alkylation of the monoalkylaromatic compound with the one or more linear alkylating agents is advantageously carried out in the presence of an acidic alkylation catalyst. Useful acidic alkylation catalysts include, by way of example, zeolite catalysts, Lewis and Brønsted acid catalysts, solid acid catalysts and the like and mixtures thereof. Suitable zeolite catalysts include natural zeolites, synthetic zeolites, and the like and mixtures thereof. In particular, zeolite, which is an inorganic crystalline porous compound containing silicon and aluminum, is a solid acid substance suitable for the present invention in terms of heat resistance and the target selectivity for cumene. Zeolite preferably has pores having approximately the same size as the molecular size of cumene and has a 6, 8, 10, 11, 12, or 14-membered ring structure, and more preferably a 12-membered ring structure. Examples of zeolite having a 12-membered ring structure include a Y type, a USY type, a mordenite type, a dealuminated mordenite type, a beta type, an MCM-22 type, and an MCM-56 type.

In one embodiment, suitable zeolites include Y zeolite, beta, SSZ-25, SSZ-26, and SSZ-33. Other possible catalysts include L zeolite, mordenite, boggsite, cloverite, VPI-5, MCM-41, MCM-36, SAPO-8, SAPO-5, MAPO-36, SAPO40, SAPO-41, MAPSO-46, CoAPO-50, hexagonal faujasite (EMC-2), gmelinite, mazzite (omega zeolite), offretite, ZSM-18, ZSM-12, Amberlyst® 36 and Amberlyst® 70. Some of these catalysts are discussed in Rosemarie Szostak's Handbook of Molecular Sieves (New York, Van Nostrand Reinhold, 1992).

In one embodiment, the acidic catalyst is an acid mordenite zeolite. Any acid mordenite zeolite may be used as the alkylation catalyst in the alkylation step, provided that the isomeric mixture is formed comprising a major amount of the para-di(alkyl-substituted)aromatic compound. A suitable acid mordenite zeolite catalyst and its preparation are described in U.S. Pat. No. 5,004,841, the contents of which are incorporated herein by reference. Typically these zeolite catalysts may be purchased from, for example, BASF, W.R. Grace & Co. and the like. Useful Lewis acid catalysts include, but are not limited to, aluminum trichloride, aluminum tribromide, aluminum triiodide, boron trifluoride, boron tribromide, boron triiodide and the like.

Useful acidic clays may be derived from naturally occurring or synthetic materials. One skilled in the art would realize that there are a number of such clays that are known to be alkylation catalysts. Examples of such acidic clays include montmorillonite, laponite, and saponite. Pillared clays may also be used as catalysts.

The catalysts used in the process of the present invention may be shaped or formed into tablets, extrudates or any other shape, such as beads, using procedures well known in the prior art. The preparation of extrudates requires the presence of a binder, such as alumina. The tableted catalysts do not require the presence of a binder, but a binder may be present in a tableted zeolite catalyst. The crystalline zeolite powder may be compressed to form a tablet.

In general, the acidic catalyst is present in an amount ranging from about 1 wt. % to about 70 wt. %, based on the total weight of the alkylation reaction mixture. In one embodiment, the acidic catalyst is present in an amount ranging from about 5 to about 50 wt. %, based on the total weight of the alkylation reaction mixture.

The reaction conditions for the alkylation depend upon the type of catalyst used, and any suitable set of reaction conditions that result in an isomeric mixture comprising a major amount of the para-di(alkyl-substituted)aromatic compound. In general, the reaction temperature will be the boiling temperature of the light solvent. In one embodiment, the reaction temperature for the alkylation reaction will be in the range of about 0° C. to about 150° C. In another embodiment, the reaction temperature for the alkylation reaction will be in the range of about 90° C. to about 140° C. The reaction pressure will generally be atmospheric, although higher or lower pressures may be employed. The alkylation process can be practiced in a batchwise, continuous or semi-continuous manner.

The molar ratio of the monoalkylaromatic compound to the one or more linear alkylating agents may vary from about 0.5:2 to about 2:0.5. In one embodiment, the molar ratio of the monoalkylaromatic compound to the one or more linear alkylating agents is in the range of about 2:1 to about 1:2. In another embodiment, the molar ratio of the monoalkylaromatic compound to the one or more linear alkylating agents is in the range of about 1.1:1 to about 1:1.1.

The residence time in the reactor is a time that is sufficient to convert a substantial portion of the one or more linear alkylating agents to a para-di(alkyl)substituted aromatic compound. In one embodiment, the time required is generally from about 2 hours to about 30 hours. A more precise residence time may be determined by those skilled in the art using batch stirred tank reactors to measure the kinetics of the alkylation process.

The alkylation reaction may be carried out neat or in the presence of a solvent which is inert to the reaction of the monoalkylaromatic compound and the one or more linear alkylating agents. When employed, a typical solvent is hexane.

Upon completion of the reaction, the desired isomeric mixture is obtained comprising a major amount of a para-di(alkyl-substituted)aromatic compound. In one embodiment, the isomeric mixture will contain about 60 mole % or greater of the para-di(alkyl-substituted)aromatic compound with the remaining isomeric mixture comprising ortho isomers of the di(alkyl-substituted)aromatic compound. In another embodiment, the isomeric mixture will contain 80 mole % or greater of the para-di(alkyl-substituted)aromatic compound with the remaining isomeric mixture comprising ortho isomers of the di(alkyl-substituted)aromatic compound. In yet another embodiment, the isomeric mixture will contain 90 mole % or greater of the para-di(alkyl-substituted)aromatic compound with the remaining isomeric mixture comprising ortho isomers of the di(alkyl-substituted)aromatic compound. In still yet another embodiment, the isomeric mixture will contain 95 mole % or greater of the para-di(alkyl-substituted)aromatic compound with the remaining isomeric mixture comprising ortho isomers of the di(alkyl-substituted)aromatic compound. In still yet another embodiment, the resulting isomeric mixture will contain 99 mole % or greater of the para-di(alkyl-substituted)aromatic compound with the remaining isomeric mixture comprising ortho isomers of the di(alkyl-substituted)aromatic compound. In one embodiment, the mixture will contain no more than about four structural isomers of para-di(alkyl-substituted) aromatic compound. In one embodiment, the mixture will contain no more than about two structural isomers of para-di(alkyl-substituted)aromatic compound.

In one embodiment, an isomeric mixture is obtained comprising a major amount of a para-di(alkyl-substituted)aromatic compound of formula I:

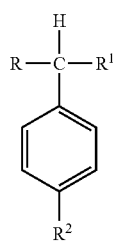

(I)

wherein R and $R^1$ are the same or different alkyl group such that the combined number of carbon atoms is no more than 8 carbon atoms, and $R^2$ is a linear alkyl group of from 4 to 50 carbon atoms, wherein $R^2$ is at least one carbon atom greater than the combined number of carbon atoms of R and $R^1$. In one embodiment, $R^2$ is a linear group derived from one or more linear normal alpha olefins as discussed hereinabove. In one embodiment, the isomeric mixture will contain no more than about four structural isomers of formula I. In one embodiment, the isomeric mixture will contain no more than about two structural isomers of formula I.

Step (b) of the process of the present invention subjects the isomeric mixture comprising a major amount of a para-di(alkyl-substituted)aromatic compound of step (a) to oxidation conditions in the presence of an oxygen-containing source, thereby converting the first alkyl substituent which is a $C_3$ to $C_8$ alkyl moiety to a hydroperoxide-containing substituted moiety to produce an isomeric mixture comprising a major amount of a para-linear alkyl-substituted, hydroperoxide-containing substituted aromatic compound.

In one embodiment, the isomeric mixture comprising a major amount of the para-di(alkyl-substituted)aromatic compound of formula I:

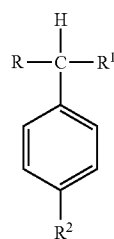

(I)

wherein R, $R^1$ and $R^2$ have the aforestated meanings, is subjected to oxidation conditions in the presence of an oxygen-containing source to produce an isomeric mixture comprising a major amount of a para-linear alkyl-substituted, hydroperoxide-containing substituted aromatic compound of formula II:

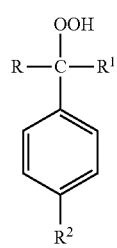

(II)

wherein R, $R^1$ and $R^2$ have the aforestated meanings. This oxidation process can take place in one or more oxidation reactor(s). The oxidation reactor(s) may be batch reactor(s) or continuous reactor(s).

The isomeric mixture comprising a major amount of the para-di(alkyl-substituted)aromatic compound is oxidized in the presence of an oxygen-containing source such as a gas, for example, air. While a solvent may be added to the isomeric mixture, oxidation is typically carried out in the absence of any solvent, other than the mixture itself.

Oxidation can also take place in the presence of at least one substituted cyclic imide of formula IV:

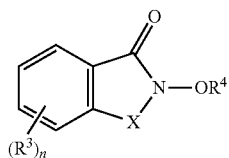

(IV)

in which X represents a carbonyl (CO) group or a sulfonyl (SO$_2$) group, n is 0, 1, 2, 3 or 4, R.sup.3 is one or several groups selected from a hydrogen atom, a halogen atom, an alkyl group, an alkoxy group, an amino group and R$^4$ is a hydrogen atom, an alkaline metal cation or an alkaline earth metal cation. Representative examples of the cyclic imide of formula (IV) include N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxysaccharin and mixtures thereof. In one embodiment, oxidation can take place in the presence of N,N',N"-trihydroxyisocyanuric acid (THICA). The cyclic imide of formula (IV) or THICA may be used in an amount of from about 0.0001 mol % to about 15 mol %, or from about 0.001 mol % to about 10 mol %, relative to the amount of the para-di(alkyl-substituted) aromatic compound.

In one embodiment, the cyclic imide of formula (IV) or THICA is used in a form in which it has been deposited or fixed chemically on a support, for example, silica, alumina, a zeolite, a polymer (e.g. polystyrene resin) or a mixture thereof.

The oxidation mixture may also include a free radical initiator, such as a peroxy compound or azo compound. Representative examples of such compounds include, but are not limited to, cumene hydroperoxide, sec-butylbenzene hydroperoxide and the like and mixtures thereof. If used, the free radical initiator can be present in an amount ranging from about 0.1 wt. % to about 5 wt. %.

Suitable oxidation conditions for step (b) include a temperature ranging from about 70° C. to about 300° C., or from about 70° C. to about 200° C., or from about 90° C. to about 30° C., or from about 100° C. to about 125° C., or from about 105° C. to about 120° C. and at a pressure of from about 101 to about 2026 kPa (about 1 to about 20 atmospheres), or from about 101 kPa to about 500 kPa (about 1 to about 5 atmospheres), or from about 101 kPa to about 150 kPa (about 1 to about 1.5 atmospheres).

A basic agent, such as an alkali metal carbonate, e.g., sodium carbonate, an alkali metal bicarbonate, e.g., sodium bicarbonate, or ammonia may also be added to react with any acidic by-products that may form during oxidation. In addition, an aqueous phase may be introduced, which can help dissolve basic compounds, such as sodium carbonate. The per-pass conversion in the oxidation step is preferably kept below 50%, to minimize the formation of byproducts. The oxidation reaction can be conveniently conducted in a catalytic distillation unit and the hydroperoxide of formula (II) produced may be concentrated by distilling off the unreacted alkylbenzene of formula (I) prior to the cleavage step.

Optionally, oxidation of the mixture may also take place in the presence of a transition metal co-catalyst, such as a cobalt, manganese or copper-containing catalyst, e.g., cobaltosic oxide (formula Co$_3$O$_4$).

Oxidation is an exothermic reaction, and the heat of reaction is removed from the oxidation reaction mixture during the reaction. For example, heat is removed by vaporization of hydrocarbon, product and water, if water is present in the oxidation mixture, into the air passing through the reactor(s). If necessary, external heat exchangers can be used to cool the vaporized products and recirculate them to the oxidation reactor(s).

In one embodiment, oxidation is carried out in an entrained flow reactor. For example, a bubble column reactor is employed. This type of reactor is well known in the field of chemical engineering. In particular, this type of reactor has multiple injection zones, which improves mass transfer.

Step (c) of the process of the present invention converts the hydroperoxide-containing substituted moiety of the para-linear alkyl-substituted, hydroperoxide-containing substituted aromatic compound to a hydroxyl moiety thereby providing an isomeric mixture comprising a major amount of a para-linear mono-alkyl-substituted hydroxyaromatic compound, i.e., the hydroperoxide-containing substituted moiety is cleaved into a hydroxyl moiety. In general, cleavage is carried out in a cleavage reactor or reactor zone, operating, for example, as a plug flow reactor, a plug flow reactor with recycle or a continuous stirred tank reactor.

This cleavage reaction is effected by contacting the isomeric mixture comprising a major amount of the para-linear alkyl-substituted, hydroperoxide-containing substituted aromatic compound in a liquid phase with a catalyst at a temperature ranging from about 20° C. to about 200° C., or from about 40° C. to about 120° C., a pressure of about 101 kPa to about 5 MPa (about 1 to about 50 atmospheres), or from about 101 kPa to 3 MPa (about 1 to about 30 atmospheres) or from about 101 kPa to about 1 MPa (about 1 to about 10 atmospheres) or from about 101 kPa to about 500 kPa (about 1 to about 5 atmospheres), and a liquid hourly space velocity (LHSV) based on the hydroperoxide of about 0.1 hr$^{-1}$ to about 10 hr$^{-1}$, or about 1 hr$^{-1}$ to about 5 hr$^{-1}$. The isomeric mixture comprising a major amount of the para-linear alkyl-substituted, hydroperoxide-containing substituted aromatic compound can be diluted in an organic solvent inert to the cleavage reaction, such as a ketone, e.g., acetone, methyl ethyl ketone and the like, to assist in heat removal. The cleavage reaction is conveniently conducted in a catalytic distillation unit.

The catalyst employed in the cleavage step can be a homogeneous catalyst or a heterogeneous catalyst. Suitable homogeneous cleavage catalysts include, but are not limited to, sulfuric acid, perchloric acid, phosphoric acid, hydrochloric acid, p-toluenesulfonic acid, ferric chloride, boron trifluoride, sulfur dioxide, sulfur trioxide and the like and mixtures thereof. In one preferred embodiment, sulfuric acid is the homogeneous cleavage catalyst. Suitable heterogeneous catalysts include a smectite clay, such as an acidic montmorillonite silica-alumina clay, as described in U.S. Pat. No. 4,870,217, the contents of which are incorporated herein by reference.

In one embodiment, the hydroperoxide-containing substituted moiety of the para-linear alkyl-substituted, hydroperoxide-containing substituted aromatic compound of formula II:

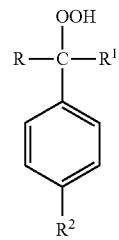

(II)

wherein R, R$^1$ and R$^2$ have the aforestated meanings is converted to a hydroxyl moiety thereby providing an isomeric mixture comprising a major amount of a para-linear monoalkyl-substituted hydroxyaromatic compound of formula III:

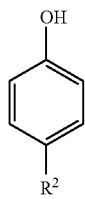
(III)

wherein $R^2$ has the aforestated meanings.

The resulting isomeric mixture obtained from the process of the present invention comprises a major amount of a para-linear mono-alkyl-substituted hydroxyaromatic compound. In one embodiment, the resulting isomeric mixture will contain about 60 mole % or greater of the para-linear mono-alkyl-substituted hydroxyaromatic compound with the remaining isomeric mixture comprising ortho isomers of the mono-alkyl-substituted hydroxyaromatic compound. In another embodiment, the resulting isomeric mixture will contain 80 mole % or greater of the para-linear mono-alkyl-substituted hydroxyaromatic compound with the remaining isomeric mixture comprising ortho isomers of the mono-alkyl-substituted hydroxyaromatic compound. In yet another embodiment, the resulting isomeric mixture will contain 90 mole % or greater of the para-linear mono-alkyl-substituted hydroxyaromatic compound with the remaining isomeric mixture comprising ortho isomers of the mono-alkyl-substituted hydroxyaromatic compound. In still yet another embodiment, the resulting isomeric mixture will contain 95 mole % or greater of the para-linear mono-alkyl-substituted hydroxyaromatic compound with the remaining isomeric mixture comprising ortho isomers of the mono-alkyl-substituted hydroxyaromatic compound. In still yet another embodiment, the resulting isomeric mixture will contain 99 mole % or greater of the para-linear mono-alkyl-substituted hydroxyaromatic compound with the remaining isomeric mixture comprising ortho isomers of the mono-alkyl-substituted hydroxyaromatic compound. In one embodiment, the resulting isomeric mixture will contain no more than about four structural isomers of the para-linear mono-alkyl-substituted hydroxyaromatic compound. In one embodiment, the resulting mixture will contain no more than about two structural isomers of the para-linear mono-alkyl-substituted hydroxyaromatic compound.

If desired, the resulting para-linear mono-alkyl-substituted hydroxyaromatic compound may be subsequently sulfurized and neutralized in any order to provide a salt of a sulfurized para-linear mono-alkyl-substituted hydroxyaromatic composition. The sulfurization and neutralization steps may be performed in any order so as to provide the salt of the sulfurized para-linear mono-alkyl-substituted hydroxyaromatic composition. Alternatively, the neutralization and sulfurization steps may be carried out simultaneously.

In general, sulfurization is carried out by contacting the para-linear mono-alkyl-substituted hydroxyaromatic compound with a sulfur source which introduces $S_x$ bridging groups between the para-linear mono-alkyl-substituted hydroxyaromatic compounds, wherein x is 1 to 7, in the presence of a base. Any suitable sulfur source can be used such as, for example, elemental sulfur or a halide thereof such as sulfur monochloride or sulfur dichloride, hydrogen sulfide, sulfur dioxide and sodium sulfide hydrates. The sulfur can be employed either as molten sulfur or as a solid (e.g., powder or particulate) or as a solid suspension in a compatible hydrocarbon liquid.

The base catalyzes the reaction to incorporate sulfur onto the para-linear mono-alkyl-substituted hydroxyaromatic compound. A suitable base includes, but is not limited to, NaOH, KOH, Ca(OH)$_2$ and the like and mixtures thereof.

The base is generally employed at from about 0.5 to about 5 moles per mole of the para-linear mono-alkyl-substituted hydroxyaromatic compound in the reaction system. In one embodiment, the base is employed at from about 1 to about 1.5 moles per mole of the para-linear mono-alkyl-substituted hydroxyaromatic compound in the reaction system. The base can be added to the reaction mixture as a solid or a liquid.

Sulfur is generally employed at from about 0.5 to about 4 moles per mole of the para-linear mono-alkyl-substituted hydroxyaromatic compound in the reaction system. In one embodiment, sulfur is employed at from about 0.8 to 2 moles per mole of the para-linear mono-alkyl-substituted hydroxyaromatic compound. In one embodiment, sulfur is employed at from about 1 to 1.5 moles per mole of para-linear mono-alkyl-substituted hydroxyaromatic compound.

The temperature range in which the sulfurization reaction is carried out is generally from about 120° C. to about 200° C. In one embodiment, the temperature range is from about 160° C. to about 180° C. The reaction can be conducted under atmospheric pressure (or slightly lower) or at elevated pressures. In one embodiment the reaction is carried out under vacuum to facilitate H$_2$S elimination. The exact pressure developed during the reaction is dependent upon such factors as the design and operation of the system, the reaction temperature, and the vapor pressure of the reactants and products and it may vary during the course of the reaction. In one embodiment, the process pressures are at atmospheric to about 20 mm Hg.

Neutralization of the sulfurized or unsulfurized para-linear mono-alkyl-substituted hydroxyaromatic compound may be carried out in a continuous or batch process by any method known to a person skilled in the art. Numerous methods are known in the art to neutralize the sulfurized or unsulfurized para-linear mono-alkyl-substituted hydroxyaromatic compounds and to produce basic phenates by incorporation of a source of base. In general, neutralization can be carried out by contacting the sulfurized or unsulfurized para-linear mono-alkyl-substituted hydroxyaromatic compound with a metal base under reactive conditions, preferably in an inert-compatible liquid hydrocarbon diluent. If desired, the reaction can be conducted under an inert gas, typically nitrogen. The metal base may be added either in a single addition or in a plurality of additions at intermediate points during the reaction.

Suitable metal basic compounds include hydroxides, oxides or alkoxides of the metal such as (1) an alkali metal salt derived from a metal base selected from an alkali hydroxide, alkali oxide or an alkali alkoxide, or (2) an alkaline earth metal salt derived from a metal base selected from an alkaline earth hydroxide, alkaline earth oxide or alkaline earth alkoxide. Representative examples of metal basic compounds with hydroxide functionality include lithium hydroxide, potassium hydroxide, sodium hydroxide, magnesium hydroxide, calcium hydroxide, barium hydroxide, aluminum hydroxide and the like. Representative examples of metal basic compounds with oxide functionality include lithium oxide, magnesium oxide, calcium oxide, barium oxide and the like. In one embodiment, the alkaline earth metal base is slaked lime (calcium hydroxide), because of its handling convenience and cost versus, for example, calcium oxide.

Neutralization is typically conducted in a suitable solvent or diluents oil, such as toluene, xylene and commonly with a promoter such as an alcohol, e.g., a $C_1$ to $C_{16}$ alcohol, such as methanol, decyl alcohol, or 2-ethyl hexanol; a diol, e.g., $C_2$ to $C_4$ alkylene glycols, such as ethylene glycol; and/or carboxylic acids. Suitable diluent oils include naphthenic oils and mixed oils, e.g. paraffinic oils such as 100 neutral oil. The quantity of solvent or diluent oil used is such that the amount of solvent or oil in the final product constitutes from about 25% to about 65% by weight of the final product, preferably from about 30% to about 50%. For example, the source of alkaline earth metal is added in excess as a slurry (i.e., as a pre-mixture of source of an alkaline earth metal lime, solvent or diluent oil) and then reacted with the sulfurized or unsulfurized para-linear mono-alkyl-substituted hydroxyaromatic compound.

The neutralization reaction between the metal base and the sulfurized or unsulfurized para-linear mono-alkyl-substituted hydroxyaromatic compound is typically conducted at temperatures above room temperature (20° C.). In one embodiment, neutralization can be carried out at a temperature between about 20° C. and about 150° C. It is however preferred to carry the neutralization at low temperature. In one embodiment, neutralization can be carried out at a temperature of between about 25° C. and about 30° C. The neutralization reaction itself should take place for a period of time of from about 5 to about 60 minutes. If desired, the neutralization reaction is carried out in the presence of a promoter such as ethylene glycol, formic acid, acetic acid, and the like and mixtures thereof.

Upon completion of the sulfurizing and neutralizing of the para-linear mono-alkyl-substituted hydroxyaromatic compound, a neutral salt of a sulfurized para-linear mono-alkyl-substituted hydroxyaromatic composition is obtained. If desired, the neutral salt of a sulfurized para-linear mono-alkyl-substituted hydroxyaromatic composition can be overbased to provide an overbased salt of a sulfurized para-linear mono-alkyl-substituted hydroxyaromatic composition. Overbasing can be carried out either during or after one of the sulfurization and neutralization steps and by any method known by a person skilled in the art. Alternatively, sulfurization, neutralization and overbasing can be carried out simultaneously. In general, the overbasing is carried out by reaction with an acidic overbasing compound such as, for example, carbon dioxide or boric acid. In one embodiment, an overbasing process is by way of carbonation, i.e., a reaction with carbon dioxide. Such carbonation can be conveniently effected by addition of solvents such as aromatic solvents, alcohols or a polyols, typically an alkylene diol, e.g., ethylene glycol. Conveniently, the reaction is conducted by the simple expedient of bubbling gaseous carbon dioxide through the reaction mixture. Excess solvents and any water formed during the overbasing reaction can be conveniently removed by distillation either during or after the reaction.

In one embodiment, the overbasing reaction is carried out in a reactor by reacting the salt of the sulfurized para-linear mono-alkyl-substituted hydroxyaromatic composition with a source of an alkaline earth metal such as lime (i.e., an alkaline earth metal hydroxide) in the presence of carbon dioxide, and in the presence of an aromatic solvent (e.g., xylene), and a hydrocarbyl alcohol such as methanol. Conveniently, the reaction is conducted by the simple expedient of bubbling gaseous carbon dioxide through the reaction mixture. The carbon dioxide may be introduced over a period of about 1 hour to about 3 hours, at a temperature ranging from about 30° C. to about 60° C. The degree of overbasing may be controlled by the quantity of the source of an alkaline earth metal, carbon dioxide and the reactants added to the reaction mixture and the reaction conditions used during the carbonation process.

In another embodiment, the overbasing reaction can be carried out between 140° C. and 180° C. in the presence of a polyol, typically an alkylene diol, e.g., ethylene glycol, and/or alkanols, e.g., $C_6$ to $C_{16}$ alkanols, such as decyl alcohols, 2-ethyl hexanol. Excess solvent and any water formed during the overbasing reaction can be conveniently removed by distillation either during or after the reaction.

The overbased salt of a sulfurized para-linear mono-alkyl-substituted hydroxyaromatic composition may have a TBN of from about 50 to about 500.

The resulting neutral or overbased salt of the sulfurized para-linear mono-alkyl-substituted hydroxyaromatic composition is advantageously employed in a lubricating oil composition comprising at least a major amount of an oil of lubricating viscosity. The lubricating oil compositions may also contain other conventional additives that can impart or improve any desirable property of the lubricating oil composition in which these additives are dispersed or dissolved. Any additive known to a person of ordinary skill in the art may be used in the lubricating oil compositions disclosed herein. Some suitable additives have been described in Mortier et al., "Chemistry and Technology of Lubricants," 2nd Edition, London, Springer, (1996); and Leslie R. Rudnick, "Lubricant Additives: Chemistry and Applications," New York, Marcel Dekker (2003), both of which are incorporated herein by reference. For example, the lubricating oil compositions can be blended with antioxidants, anti-wear agents, detergents such as metal detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and the like and mixtures thereof. A variety of the additives are known and commercially available. These additives, or their analogous compounds, can be employed for the preparation of the lubricating oil compositions of the invention by the usual blending procedures.

The following non-limiting examples are illustrative of the present invention.

In the examples, 1-dodecene and cumene were purchased from Fluka and Acros, respectively, and used as received. The $C_{20}$-$C_{24}$ NAO blend was from ChevronPhillips Company LLC, Cedar Bayou, Tex. The mordenite extrudates were from Engelhardt (now BASF, SAR=100, alumina binder) and were pre-dried (approximately 140° C.) overnight prior to use. The NMR experiments were performed on Bruker Advance III. Deuterated solvents for NMR were purchased from ACROS and stored under nitrogen upon receiving. GC/MS analytical experiments were run on a Hewlett Packard 5973 GC-Mass selective detector equipped with a Zebron capillary GC column ZB-1HT Inferno 15 m (length)×0.25 mm (I.D)×0.10 μM (thickness).

EXAMPLE 1

Reactions were performed in a round bottom neck flask equipped with a reflux condenser. According to the experimental procedure described in U.S. Pat. No. 5,468,407, a mixture of Mordenite (6.55 g), cumene (2.76 g, 2.25 mmol) and 1-dodecene (3.79 g, 2.25 mmol) was heated at 140° C. for 6 h. The reaction mixture was then cooled down to room temperature and filtrated to afford 3 mL of a colorless solution. Mordenite extrudates were further washed for 5 mins with 10 mL of acetone. The organic phases were then combined and concentrated under vacuum (rotovap) to afford ≈7 mL of a mixture composed of p-(2-dodecyl)cumene (88%), p-(3-dodecyl)cumene (3%) and o-(2-dodecyl)cumene (9%) as determined by GC (98% conversion).

EXAMPLE 2

Preparation of Alkylcumene Hydroperoxide

Into a three-neck round bottom flask was added 15.39 g of the p-(2-dodecyl)cumene of Example 1 followed by 0.3 g of cumene hydroperoxide. After 5 min of mixing 0.54 g of cobaltosic oxide was added to the mixture with vigorous stirring. The flask was sealed in an entrained flow reactor system and oxygen was introduced through a sparger at 100 sccm rate. The flask was then placed into a preheated oil bath. The mixture was heated to 97° C. in 15 min and kept at this temperature for 4 hrs. During the reaction, small kinetic samples were withdrawn from the flask periodically to monitor the conversion by FTIR. Upon completion, the flask was cooled down to room temperature under oxygen. The liquid products were separated from the catalyst by filtration and analyzed by FTIR, and NMR. The product was used for the next step without further purification.

EXAMPLE 3

Acid Cleavage of Alkylcumene Hydroperoxide to Alkylphenol

The reaction was carried out in 100 ml round bottom flask under agitation with a magnetic stirrer. The flask had an addition funnel and a distillation link with Liebig condenser and a receiver flask attached to it. A catalyst mixture was first prepared by adding 0.5 ml of water to 50 ml of acetone followed by 2 ml of concentrated sulfuric acid. Next, 25 ml of the mixture was transferred into the round bottom flask. The flask was heated up in a water bath to 50° C., the temperature which is close to a boiling point of the mixture. Next, 8 ml of product obtained by the procedure of the Example 2 was mixed with 8 ml of acetone. The mixture was placed into the addition funnel and added slowly to the flask containing the acid catalyst. The acetone was distilled out from the flask. The temperature was slowly increased to 60° C. to assure the completeness of the reaction. The reaction product was analyzed by NMR and GC/MS. $^1H$ and $^{13}C$ NMR experiments (chemical shift and peak patterns), mass fragmentation pattern and retention time comparison with known samples confirm a 77/23 ratio of para-$C_{12}/C_3$ alkylphenols (15-20% conversion from the alkylcumene product). No ortho-alkylphenols were observed in the GC/MS or the IR analysis.

EXAMPLE 4

Following the general procedure described in Example 1, 35.8 g (0.29 mol) of cumene reacted with 79.9 g of a $C_{20}$ to $C_{24}$ mixture of normal alpha-olefins (0.27 mol) in presence of 115 g of mordenite to give, after 22 h, 66 g of the corresponding $C_{20}$ to $C_{24}$ alkylcumenes in a 5/95 o,p mixture (99% conversion).

Based on the chemical properties of the product obtained in Example 4, we believe that the subsequent oxidation and decomposition steps as per Examples 2 and 3, respectively, would afford an alkylphenol mixture with an enhanced para-isomer content.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A process for preparing an isomeric mixture comprising a major amount of a para-linear mono-alkyl-substituted hydroxyaromatic compound, the process comprising the steps of:
   (a) providing an isomeric mixture comprising a major amount of a para-di(alkyl-substituted)aromatic compound; wherein a first alkyl substituent is a $C_3$ to $C_8$ alkyl moiety and a second alkyl substituent is a $C_{4+n}$ to $C_{8+n}$ linear alkyl moiety, wherein n is 0 to 42 and further wherein the second alkyl substituent is at least one carbon atom greater than the first alkyl substituent,
   (b) subjecting the isomeric mixture comprising a major amount of a para-di(alkyl-substituted)aromatic compound to oxidation conditions in the presence of an oxygen-containing source, thereby converting the first alkyl substituent which is a $C_3$ to $C_8$ alkyl moiety to a hydroperoxide-containing substituted moiety to produce an isomeric mixture comprising a major amount of a para-linear alkyl-substituted, hydroperoxide-containing substituted aromatic compound; and
   (c) converting the hydroperoxide-containing substituted moiety to a hydroxyl moiety thereby providing an isomeric mixture comprising a major amount of a para-linear mono-alkyl-substituted hydroxyaromatic compound.

2. The process of claim 1, wherein the second alkyl substituent is derived from a $C_4$ to $C_{50}$ linear normal alpha olefin.

3. The process of claim 1, wherein the isomeric mixture of step (a) is obtained from the reaction of a monoalkylaromatic compound and one or more linear alkylating agents in the presence of an acidic catalyst.

4. The process of claim 3, wherein the one or more linear alkylating agents is a $C_4$ to $C_{50}$ linear normal alpha olefin.

5. The process of claim 3, wherein the acidic catalyst is an acidic zeolite catalyst.

6. The process of claim 3, the molar ratio of the monoalkylaromatic compound to the one or more linear alkylating agents is in the range of about 0.5:2 to about 2:0.5.

7. The process of claim 1, wherein the oxygen-containing source is air.

8. The process of claim 1, wherein step (b) is carried out in the presence of a free radical initiator.

9. The process of claim 8, wherein the free radical initiator is a peroxy compound or azo compound.

10. The process of claim 1, wherein the oxidation conditions for step (b) comprise a temperature ranging from about 70° C. to about 200° C.

11. The process of claim 1, wherein step (c) is carried out in the presence of a catalyst.

12. The process of claim 11, wherein the catalyst is selected from the group consisting, of sulfuric acid, perchloric acid, phosphoric acid, hydrochloric acid, p-toluenesulfonic acid, ferric chloride, boron trifluoride, sulfur dioxide and sulfur trioxide.

13. The process of claim 1, wherein the isomeric mixture contains about 60 mole % or greater of the para-linear mono-alkyl-substituted hydroxyaromatic compound with the remaining isomeric mixture comprising ortho isomers of the mono-alkyl-substituted hydroxyaromatic compound.

14. The process of claim 1, wherein the isomeric mixture contains about 80 mole % or greater of the para-linear mono-alkyl-substituted hydroxyaromatic compound with the remaining isomeric mixture comprising ortho isomers of the mono-alkyl-substituted hydroxyaromatic compound.

15. The process of claim 1, wherein the isomeric mixture contains about 90 mole % or greater of the para-linear mono-alkyl-substituted hydroxyaromatic compound with the remaining isomeric mixture comprising ortho isomers of the mono-alkyl-substituted hydroxyaromatic compound.

16. The process of claim 1, wherein the isomeric mixture contains about 95 mole % or greater of the para-linear mono-alkyl-substituted hydroxyaromatic compound with the remaining isomeric mixture comprising ortho isomers of the mono-alkyl-substituted hydroxyaromatic compound.

17. The process of claim 1, wherein the isomeric mixture contains about 99 mole % or greater of the para-linear mono-alkyl-substituted hydroxyaromatic compound with the remaining isomeric mixture comprising ortho isomers of the mono-alkyl-substituted hydroxyaromatic compound.

18. A process comprising the steps of:
(a) providing an isomeric mixture comprising a major amount of a para-di(alkyl-substituted)aromatic compound of formula I:

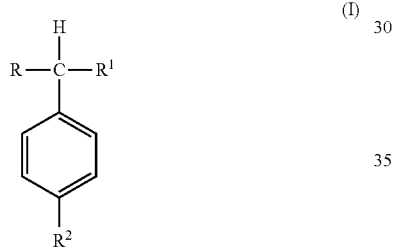

(I)

wherein R and $R^1$ are the same or different alkyl group such that the combined number of carbon atoms is no more than 8 carbon atoms, and $R^2$ is a linear alkyl group of from 4 to 50 carbon atoms, wherein $R^2$ is at least one carbon atom greater than the combined number of carbon atoms of R and $R^1$;
(b) subjecting the isomeric mixture comprising a major amount of the para-di(alkyl-substituted)aromatic compound of formula I to oxidation conditions in the presence of an oxygen-containing source to produce an isomeric mixture comprising a major amount of a para-linear alkyl-substituted hydroperoxide-containing substituted aromatic compound of formula II:

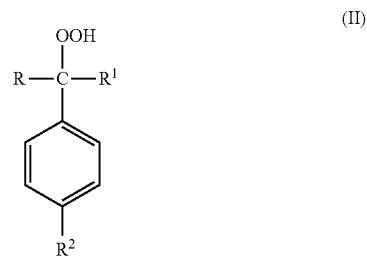

(II)

wherein R, $R^1$ and $R^2$ have the aforestated meanings; and
(c) converting the hydroperoxide-containing substituted moiety of the para-linear alkyl substituted hydroperoxide-containing substituted aromatic compound of formula II to a hydroxyl moiety thereby providing an isomeric mixture comprising a major amount of a para-linear mono-alkyl-substituted hydroxyaromatic compound of formula III:

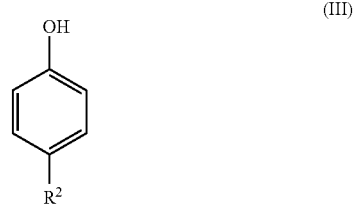

(III)

wherein $R^2$ has the aforestated meaning.

19. The process of claim 18, wherein step (b) is carried out in the presence of a free radical initiator and step (c) is carried out in the presence of a catalyst.

20. The process of claim 18, wherein the oxidation conditions for step (b) comprise a temperature ranging from about 70° C. to about 300° C.

21. The process of claim 18, wherein the isomeric mixture contains about 95 mole % is or greater of the para-linear mono-alkyl-substituted hydroxyaromatic compound with the remaining isomeric mixture comprising oho isomers of the mono-alkyl-substituted hydroxyaromatic compound.

* * * * *